US012778802B2

(12) United States Patent
Ootsuki

(10) Patent No.: US 12,778,802 B2
(45) Date of Patent: Nov. 3, 2026

(54) CONTROL APPARATUS, CONTROL METHOD, AND OPHTHALMIC SURGICAL SYSTEM

(71) Applicant: SONY GROUP CORPORATION, Tokyo (JP)

(72) Inventor: Tomoyuki Ootsuki, Tokyo (JP)

(73) Assignee: SONY GROUP CORPORATION, Tokyo (JP)

(*) Notice: Subject to any disclaimer, the term of this patent is extended or adjusted under 35 U.S.C. 154(b) by 792 days.

(21) Appl. No.: 18/042,025

(22) PCT Filed: Aug. 17, 2021

(86) PCT No.: PCT/JP2021/030040
§ 371 (c)(1),
(2) Date: Feb. 17, 2023

(87) PCT Pub. No.: WO2022/050043
PCT Pub. Date: Mar. 10, 2022

(65) Prior Publication Data

US 2023/0320899 A1 Oct. 12, 2023

(30) Foreign Application Priority Data

Sep. 1, 2020 (JP) ................................ 2020-147006

(51) Int. Cl.
*A61F 9/008* (2006.01)
*A61F 9/007* (2006.01)

(52) U.S. Cl.
CPC .......... *A61F 9/008* (2013.01); *A61F 9/00736* (2013.01); *A61F 2009/00851* (2013.01); *A61F 2009/0087* (2013.01)

(58) Field of Classification Search
CPC ........ A61F 9/00736; A61F 2009/00844; A61F 9/00745; A61F 9/008; A61F 2009/00851;
(Continued)

(56) References Cited

U.S. PATENT DOCUMENTS

2009/0137993 A1* 5/2009 Kurtz .................. A61F 9/00825 606/6
2009/0306581 A1* 12/2009 Claus ..................... A61B 90/20 604/22
(Continued)

FOREIGN PATENT DOCUMENTS

CN 103431941 A 12/2013
CN 104997587 A 10/2015
(Continued)

OTHER PUBLICATIONS

International Search Report and Written Opinion of PCT Application No. PCT/JP2021/030040, issued on Nov. 9, 2021, 10 pages of ISRWO.

*Primary Examiner* — Philip R Wiest
*Assistant Examiner* — Meagan Ngo
(74) *Attorney, Agent, or Firm* — CHIP LAW GROUP

(57) ABSTRACT

Provided is a control apparatus that includes an acquisition unit and a control unit. The acquisition unit acquires situation information relating to surgery, the situation information being based on a captured image relating to a patient eyeball, the captured image being captured by a surgical microscope. The control unit controls a control parameter relating to a treatment apparatus on the basis of the situation information, the treatment apparatus being used for the surgery.

15 Claims, 11 Drawing Sheets

(58) Field of Classification Search
CPC .... A61F 2009/0087; A61F 2009/00874; A61F 9/00821; A61F 2009/00863; A61B 3/13
See application file for complete search history.

(56) References Cited

U.S. PATENT DOCUMENTS

| | | | | |
|---|---|---|---|---|
| 2013/0226072 | A1* | 8/2013 | Kraus | A61F 9/00745 604/22 |
| 2014/0171959 | A1 | 6/2014 | Yacono | |
| 2016/0331584 | A1* | 11/2016 | Ren | A61B 34/25 |
| 2018/0098812 | A1* | 4/2018 | Ootsuki | A61B 90/25 |
| 2019/0015167 | A1* | 1/2019 | Draelos | A61B 34/76 |
| 2019/0038364 | A1* | 2/2019 | Enoki | A61B 3/13 |
| 2019/0262175 | A1* | 8/2019 | Kerkhoff | A61F 9/00745 |
| 2020/0163727 | A1* | 5/2020 | Patton | A61F 9/008 |
| 2022/0104884 | A1* | 4/2022 | Leiderman | A61F 9/00736 |

FOREIGN PATENT DOCUMENTS

| | | | |
|---|---|---|---|
| JP | 2005-013425 | A | 1/2005 |
| JP | 2007-530153 | A | 11/2007 |
| JP | 2013-540511 | A | 11/2013 |
| JP | 2019-534127 | A | 11/2019 |
| KR | 20140104586 | A | 8/2014 |

* cited by examiner

CONTROL APPARATUS, CONTROL METHOD, AND OPHTHALMIC SURGICAL SYSTEM

CROSS REFERENCE TO RELATED APPLICATIONS

This application is a U.S. National Phase of International Patent Application No. PCT/JP2021/030040 filed on Aug. 17, 2021, which claims priority benefit of Japanese Patent Application No. JP 2020-147006 filed in the Japan Patent Office on Sep. 1, 2020. Each of the above-referenced applications is hereby incorporated herein by reference in its entirety.

TECHNICAL FIELD

The present technology relates to a control apparatus, a control method, a program, and an ophthalmic surgical system that can be applied to a surgical apparatus used for ophthalmic medicine and the like.

BACKGROUND ART

In an ultrasonic surgical apparatus described in Patent Literature 1, ultrasonic power of an ultrasonic chip that fragments a lens nucleus of a patient eyeball, which is changed by operating a foot switch, is set to be a predetermined value. Moreover, hardness of the lens nucleus of the patient eyeball is determined on the basis of a usage time of ultrasonic vibration. In accordance with the determined hardness of the lens nucleus, the set value of the ultrasonic power is switched. Accordingly, efficient surgery is achieved (paragraphs [0016] and [0027], FIGS. 6A and 6B, and the like in Patent Literature 1).

CITATION LIST

Patent Literature

Patent Literature 1: Japanese Patent Application Laid-open No. 2005-013425

DISCLOSURE OF INVENTION

Technical Problem

In ophthalmic surgery such as cataract surgery, there are a scene where quick procedures are performed and a scene where fine procedures, e.g., avoiding damage of a posterior capsule or the like are required. Therefore, for a surgical apparatus (treatment apparatus) for ophthalmology, it is desirable to provide a technology by which precise control can be made efficiently.

In view of the above-mentioned circumstances, it is an objective of the present technology to provide a control apparatus, a control method, a program, and an ophthalmic surgical system by which precise control is made efficiently.

Solution to Problem

In order to accomplish the above-mentioned objective, a control apparatus according to an embodiment of the present technology includes an acquisition unit and a control unit.

The acquisition unit acquires situation information relating to surgery, the situation information being based on a captured image relating to a patient eyeball, the captured image being captured by a surgical microscope.

The control unit controls a control parameter relating to a treatment apparatus on the basis of the situation information, the treatment apparatus being used for the surgery.

In this control apparatus, the situation information relating to the surgery that is based on the captured image relating to the patient eyeball that is captured by the surgical microscope is acquired. The control parameter relating to the treatment apparatus used for the surgery is controlled on the basis of the situation information. Accordingly, precise control can be made efficiently.

A control method according to an embodiment of the present technology is a control method that is executed by a computer system and includes acquiring situation information relating to surgery, the situation information being based on a captured image relating to a patient eyeball, the captured image being captured by a surgical microscope.

A control parameter relating to a treatment apparatus used for the surgery on the basis of the situation information is controlled.

A program according to an embodiment of the present technology causes a computer system to execute the following steps.

A step of acquiring situation information relating to surgery, the situation information being based on a captured image relating to a patient eyeball captured by a surgical microscope.

A step of controlling a control parameter relating to a treatment apparatus used for the surgery on the basis of the situation information.

An ophthalmic surgical system according to an embodiment of the present technology includes a surgical microscope, a treatment apparatus, and a control apparatus.

The surgical microscope is capable of capturing an image of a patient eyeball.

The treatment apparatus is used for surgery of the patient eyeball.

The control apparatus includes an acquisition unit that acquires situation information relating to the surgery, the situation information being based on a captured image relating to the patient eyeball captured by a surgical microscope, and a control unit that controls a control parameter relating to the treatment apparatus on the basis of the situation information.

MODE(S) FOR CARRYING OUT THE INVENTION

Hereinafter, embodiments according to the present technology will be described with reference to the drawings.

First Embodiment

[Configuration Example of Surgical System]

Figure 1:
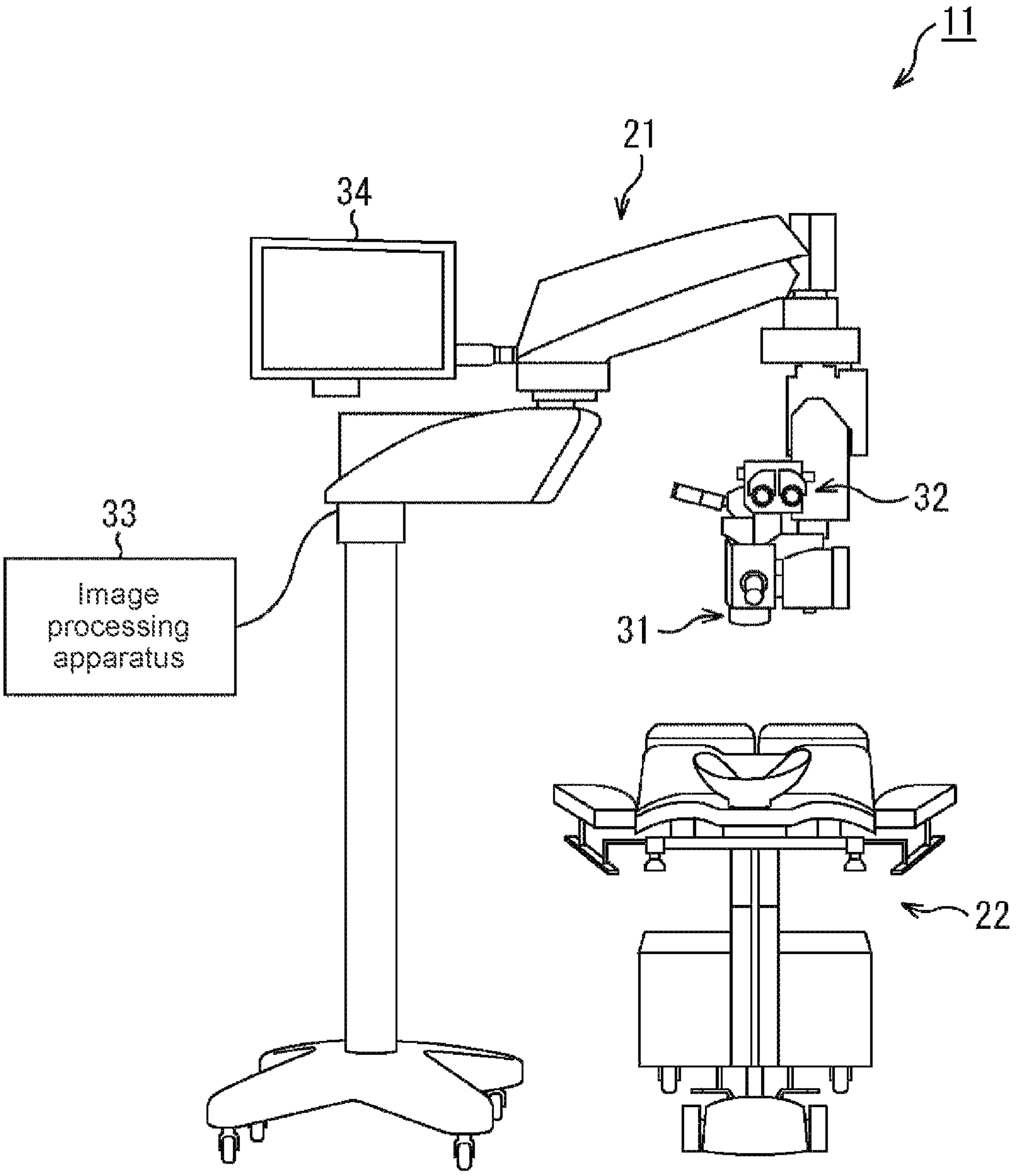
FIG. 1 A diagram schematically showing a configuration example of a surgical system.

FIG. 1 is a diagram schematically showing a configuration example of a surgical system according to a first embodiment of the present technology.

A surgical system 11 is a system used for surgery of an eyeball. In FIG. 1, the surgical system 11 has a surgical microscope 21 and a patient bed 22. Moreover, the surgical system 11 includes a treatment apparatus (not shown).

The treatment apparatus is an apparatus used for ophthalmic medicine. In the present embodiment, the surgical system 11 includes a treatment apparatus used for cataract surgery or vitreous removal. Alternatively, the surgical system 11 may include an arbitrary apparatus used for surgery.

The surgical microscope 21 has an objective lens 31, an eyepiece 32, an image processing apparatus 33, and a monitor 34.

The objective lens 31 is for magnifying and observing a patient eyeball that is a surgery target.

The eyepiece 32 collects light reflected from the patient eyeball and forms an optical image of the patient eyeball.

The image processing apparatus 33 controls the operation of the surgical microscope 21. For example, the image processing apparatus 33 is capable of acquiring images captured via the objective lens 31, lighting up a light source, changing a zoom scale, and the like.

The monitor 34 displays images captured via the objective lens 31 and physical information such as a patient pulse.

A user (e.g., a surgeon) is able to look through the eyepiece 32, observe the patient eyeball via the objective lens 31, and perform surgery using the treatment apparatus (not shown).

Figure 2:
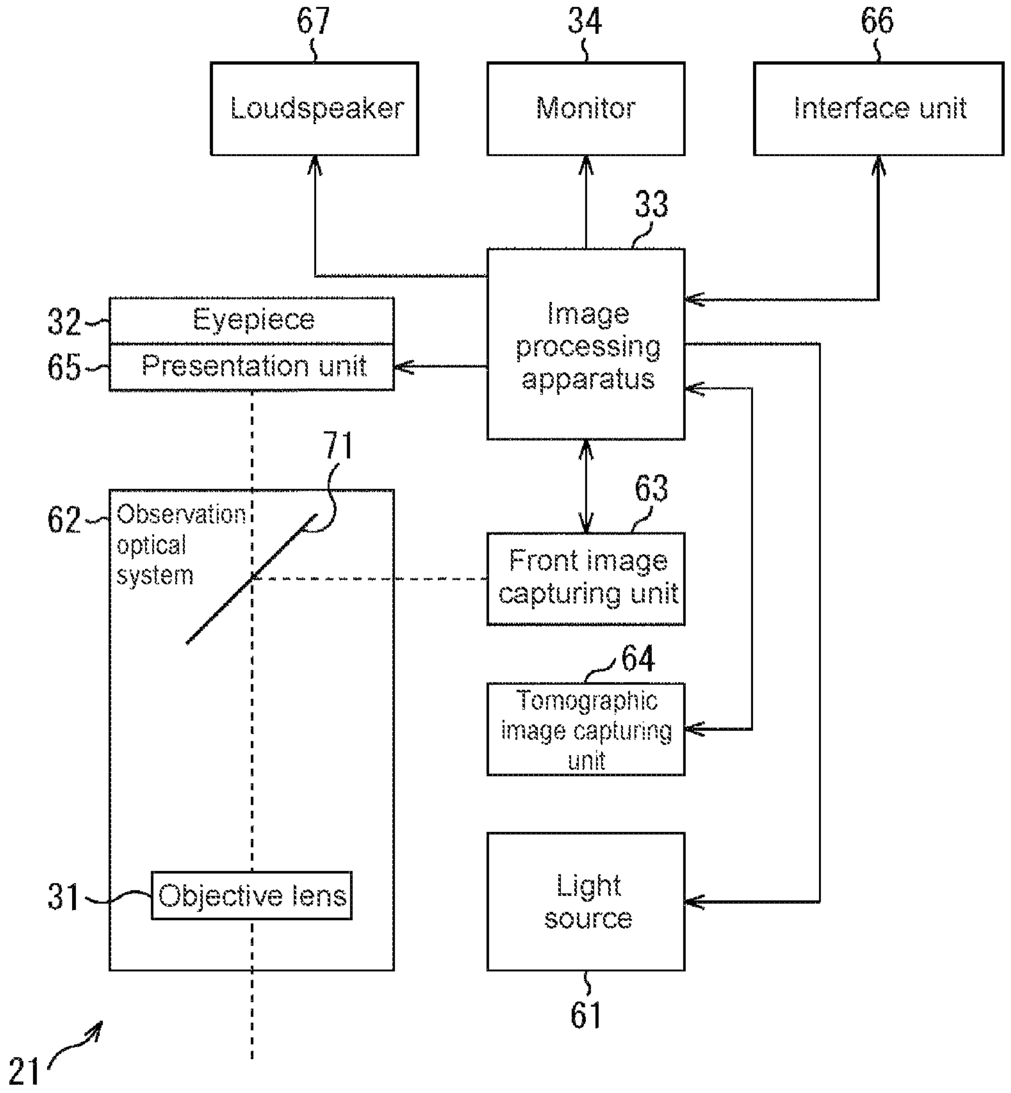
FIG. 2 A block diagram showing a configuration example of the surgical microscope.

FIG. 2 is a block diagram showing a configuration example of the surgical microscope 21.

As shown in FIG. 2, the surgical microscope 21 has the objective lens 31, the eyepiece 32, the image processing apparatus 33, the monitor 34, a light source 61, an observation optical system 62, a front image capturing unit 63, a tomographic image capturing unit 64, a presentation unit 65, an interface unit 66, and a loudspeaker 67.

The light source 61 emits illumination light and illuminates the patient eyeball. For example, the image processing apparatus 33 controls the amount of illumination light and the like.

The observation optical system 62 guides light reflected from the patient eyeball to the eyepiece 32 and the front image capturing unit 63. A configuration of the observation optical system 62 is not limited, and the observation optical system 62 may be constituted by the objective lens 31, a half mirror 71, and an optical element such as a lens (not shown).

For example, the light reflected from the patient eyeball is made incident on the half mirror 71 via the objective lens 31 and the lens. An approximately half of the light made incident on the half mirror 71 passes through the half mirror 71 and is made incident on the eyepiece 32 via the presentation unit 65. Moreover, the other approximately half of the light is reflected on the half mirror 71 and made incident on the front image capturing unit 63.

The front image capturing unit 63 captures a front image that is an image obtained when observing the patient eyeball from the front. For example, the front image capturing unit 63 is an image capturing apparatus such as a video microscope. Moreover, the front image capturing unit 63 captures a front image by receiving light made incident from the observation optical system 62 and photoelectrically converting it. For example, the front image is an image obtained by capturing an image of the patient eyeball in a direction approximately identical to an eyeball axial direction.

The captured front image is supplied to the image processing apparatus 33 and an image acquisition unit 81 to be described later.

The tomographic image capturing unit 64 captures a tomographic image that is an image of a cross-section of the patient eyeball. For example, the tomographic image capturing unit 64 is an optical coherence tomography (OCT) or Scheimpflug camera. Here, the tomographic image refers to an image of a cross-section in a direction approximately parallel to the eyeball axial direction of the patient eyeball.

The captured tomographic image is supplied to the image processing apparatus 33 and the image acquisition unit 81 to be described later.

The presentation unit 65 is constituted by a see-through display device. The presentation unit 65 is arranged between the eyepiece 32 and the observation optical system 62. The presentation unit 65 transmits light made incident from the observation optical system 62 therethrough and makes it incident on the eyepiece 32. Moreover, the presentation unit 65 may superimpose the front image and the tomographic image supplied from the image processing apparatus 33 on the optical image of the patient eyeball or display them in a periphery of the optical image.

The image processing apparatus 33 is capable of performing predetermined processing on the front image and the tomographic image supplied from the front image capturing unit 63 and the tomographic image capturing unit 64. Moreover, the image processing apparatus 33 controls the light source 61, the front image capturing unit 63, the tomographic image capturing unit 64, and the presentation unit 65 on the basis of user operation information supplied from the interface unit 66.

The interface unit 66 is an operation device such as a controller. For example, the interface unit 66 supplies the user operation information to the image processing apparatus 33. Moreover, the interface unit 66 may include a communication unit capable of communication with an external apparatus.

Figure 3:
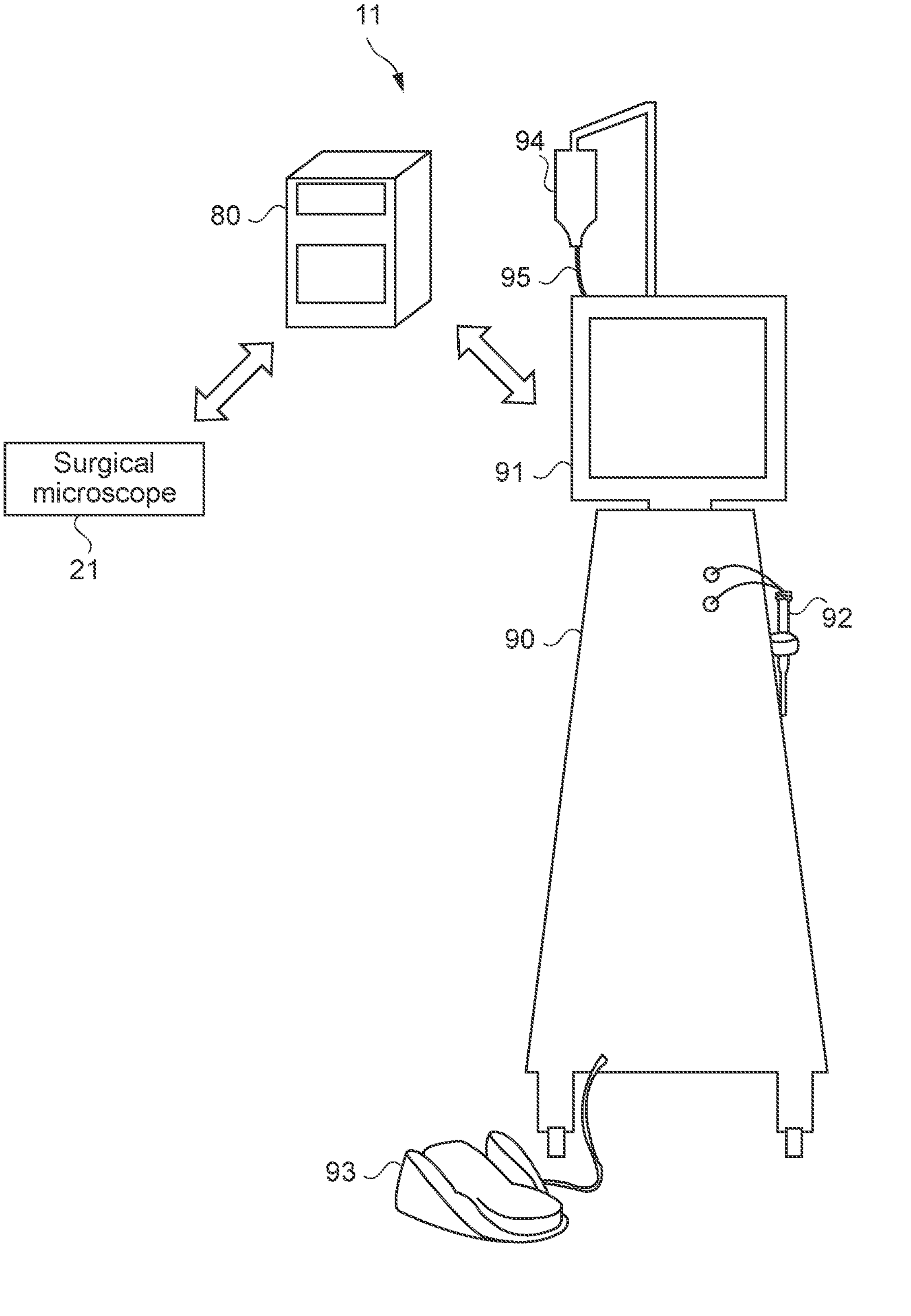
FIG. 3 A diagram schematically showing a configuration example of the surgical system.

FIG. 3 is a diagram schematically showing a configuration example of the surgical system 11.

As shown in FIG. 3, the surgical system 11 has the surgical microscope 21, the control apparatus 80, and a phaco machine 90. The surgical microscope 21, the control apparatus 80, and the phaco machine 90 are connected to be capable of communicating with each other with a wire or wirelessly. A connection form between the devices is not limited, and for example, can use wireless LAN communication such as Wi-Fi or near-field communication such as Bluetooth (registered trademark).

The control apparatus 80 recognizes situation information relating to the surgery on the basis of a captured image relating to the patient eyeball, the captured image being captured by the surgical microscope 21. Moreover, the control apparatus 80 controls a control parameter relating to the treatment apparatus used for surgery on the basis of the situation information. For example, in FIG. 3, the situation information is recognized on the basis of the front image and the tomographic image acquired from the surgical microscope 21. That is, the captured image includes the front image and the tomographic image.

The situation information is various types of information relating to surgery performed on the patient eyeball. In the present embodiment, the situation information includes a phase of the surgery. For example, as shown in FIG. 4, in a case where cataract surgery (phacoemulsification) is performed on a patient eyeball, it is divided into the following phases.

Figure 4:
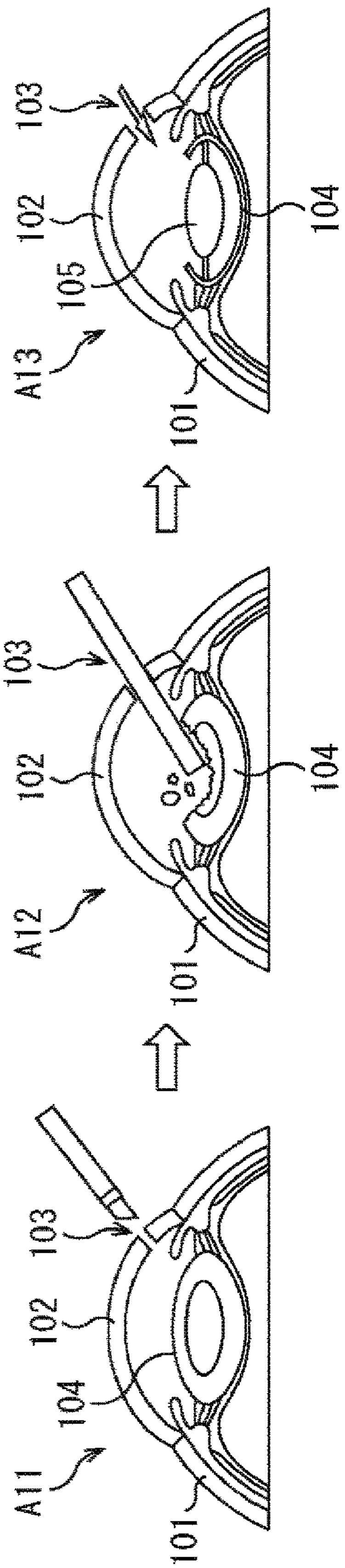
FIG. 4 A diagram describing cataract surgery briefly.

Cornea portion incision: as shown in the arrow A11 of FIG. 4, a phase where a cornea portion 102 of a patient eyeball 101 is cut with a scalpel or the like and an incision 103 is made.

Anterior capsule incision: a phase where a surgical instrument is inserted through the incision 103 portion and an anterior capsule portion of a lens 104 is cut in a circular shape.

Fragmentation of a lens nucleus: as shown in the arrow A12 of FIG. 4, a surgical instrument is inserted into the cut anterior capsule portion of the lens 104*f* through the incision 103 and fragmentation (emulsification) of a nucleus of the lens 104 is performed by ultrasonic vibration. In the present embodiment, it is divided into a phase (first phase) where a predetermined amount or more of the nucleus of the lens 104 remains and a phase (second phase) where a predetermined amount or less of the nucleus of the lens 104 remains.

Aspiration through a surgical instrument distal end: a phase where aspiration is performed using a surgical instrument. In the present embodiment, waste of the patient eyeball 101 is aspirated through the surgical instrument distal end. The waste is a tissue of the patient eyeball aspirated during surgery, such as the fragmented nucleus of the lens 104, perfusion solution, and a cortex, for example. Moreover, the "aspiration through the surgical instrument distal end" may be performed at the same time as the "fragmentation of the lens nucleus".

Insertion of an intraocular lens: as shown in the arrow A13 of FIG. 4, an intraocular lens 105 is inserted into the lens 104.

It should be noted that each of the above-mentioned phases may be divided into further phases. For example, in accordance with a residual amount of the lens nucleus in the "fragmentation of the lens nucleus", the phase may be set to be a phase 1, a phase 2, a phase 3, and the like. Hereinafter, more detailed phases of a phase will be referred to as fragmentation 1 of the lens nucleus and fragmentation 2 of the lens nucleus, for example.

It should be noted that the phases of the surgery are not limited and phases other than the above-mentioned phases may be arbitrarily changed in accordance with each surgeon. As a matter of course, surgical instruments and surgical techniques to be used may be changed in accordance with a disease. Moreover, a local anesthesia phase and the like may be set.

The control parameter includes at least one of a parameter relating to an ultrasonic output, a parameter relating to aspiration through the surgical instrument distal end, or a parameter relating to an inflow of the perfusion solution.

The parameter relating to the ultrasonic output is a parameter indicating an ultrasonic output for fragmenting the nucleus of the lens 104 of the patient eyeball 101. For example, in a case where it is desirable to fragment the lens 104 quickly, the ultrasonic output is output at a maximum value.

The parameter relating to aspiration through the surgical instrument distal end is a parameter indicating a pressure or amount of aspiration when performing aspiration through the surgical instrument. For example, in a case where it is desirable to prevent the surgical instrument that aspirates the waste from suctioning the posterior capsule, the pressure or amount of aspiration during the aspiration is controlled to be low.

The parameter relating to the inflow of the perfusion solution is a parameter indicating an inflow when causing the perfusion solution to flow in. For example, in order to maintain the eyeball internal pressure of the patient eyeball 101 at a predetermined value, the amount of perfusion solution is controlled. Moreover, the parameter relating to the inflow of the perfusion solution also includes a height of a container (bottle 94) filled with the perfusion solution.

A phacoemulsification machine (phaco machine) 90 is a treatment apparatus used for cataract surgery and an arbitrary configuration is provided. For example, the phaco machine 90 has a display unit 91, a fragmentation unit 92, a foot switch 93, and a bottle 94 as main components in FIG. 3.

The display unit 91 displays various types of information relating to the cataract surgery. For example, the current ultrasonic output, the pressure of aspiration of the waste, or the front image is displayed.

The fragmentation unit 92 is a surgical instrument that outputs an ultrasonic wave for fragmenting the nucleus of the lens of the patient eyeball. Moreover, the fragmentation unit 92 is provided with an aspiration hole for aspirating the waste and is capable of aspirating the perfusion solution and the emulsified nucleus of the lens 104.

Moreover, the fragmentation unit 92 is capable of causing the perfusion solution to flow in the patient eyeball. In the present embodiment, the perfusion solution in the bottle 94 is caused to flow in the patient eyeball via a perfusion tube 95.

The foot switch 93 controls the ultrasonic output, the pressure of aspiration of the waste, and the inflow of the perfusion solution in accordance with an amount of depression of the pedal.

The bottle 94 is a container filled with perfusion solution such as saline solution to be supplied to the patient eyeball. The bottle 94 is connected to the perfusion tube 95 for guiding the perfusion solution to the patient eyeball. Moreover, the bottle 94 has a configuration capable of changing the height and the height is adjusted to maintain the eyeball internal pressure of the patient eyeball at an appropriate pressure.

Alternatively, the phaco machine 90 may have an arbitrary configuration. For example, the bottle 94 may be built in the phaco machine 90 and a pump or the like for controlling the inflow of the perfusion solution may be mounted. Moreover, for example, an apparatus for causing the perfusion solution to flow in the patient eyeball may be provided.

Figure 5:
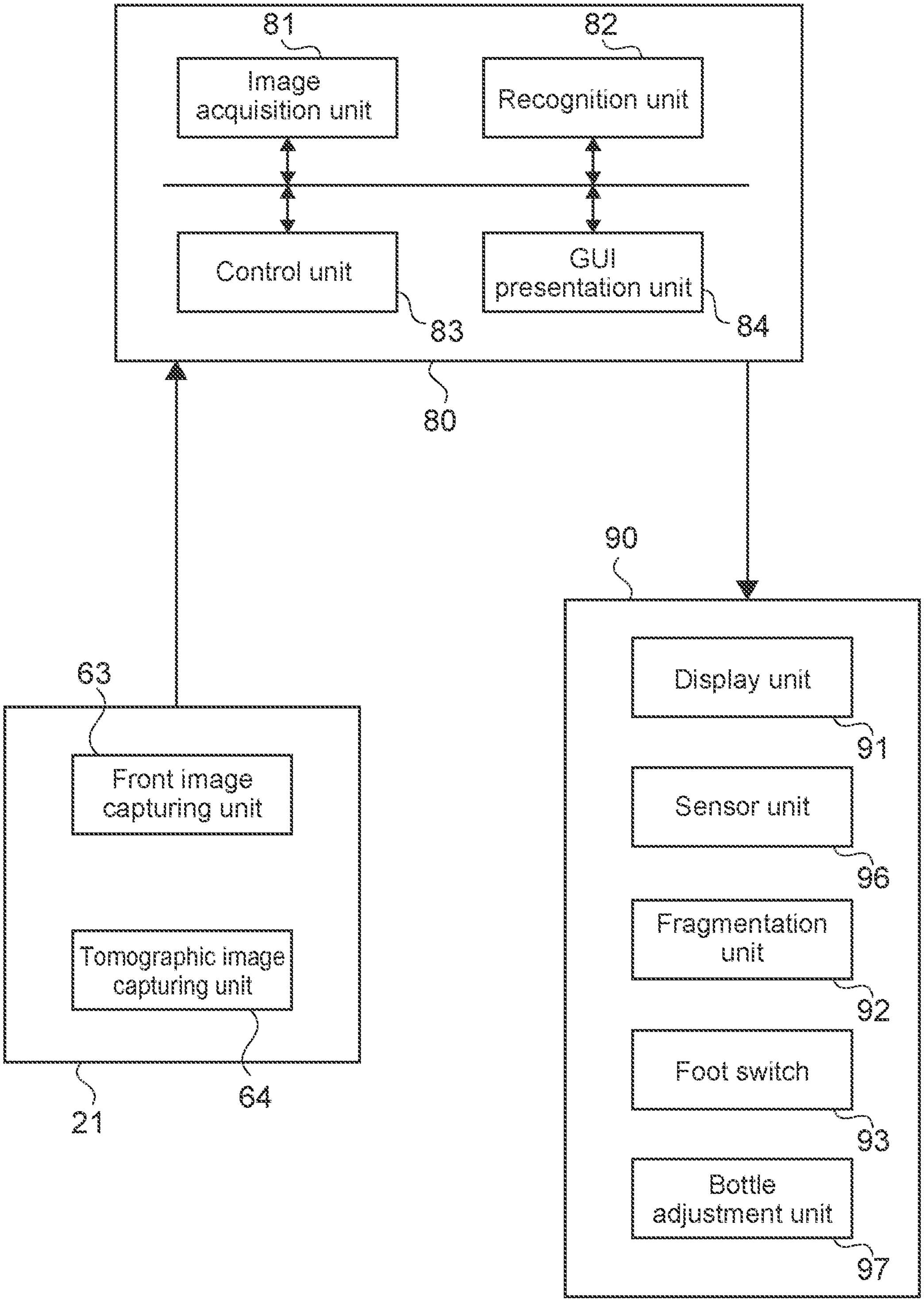
FIG. 5 A block diagram schematically showing a functional configuration example of the surgical system.

FIG. 5 is a block diagram schematically showing a functional configuration example of the surgical system 11. In FIG. 5, for the sake of simplification, only a part of the surgical microscope 21 is shown.

Figure 11:
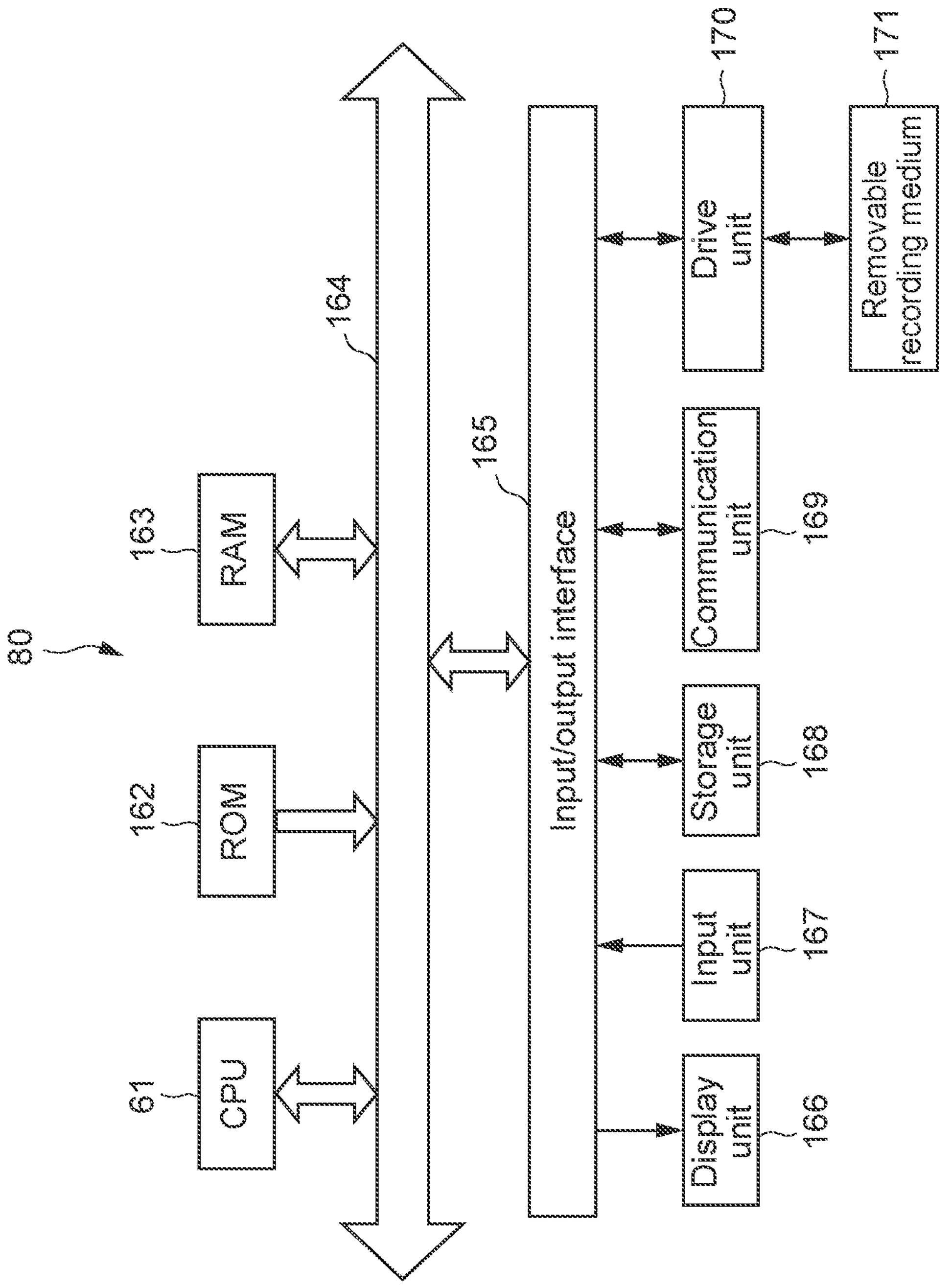
FIG. 11 A block diagram showing a hardware configuration example of a control apparatus.

The control apparatus 80 has, for example, hardware required for a computer configuration, which includes a processor such as a CPU, a GPU, and a DSP, a memory such as a ROM and a RAM, and a storage device such as an HDD (see FIG. 11). A control method according to the present technology is performed by, for example, the CPU loading a program according to the present technology recorded in the ROM or the like in advance into the RAM and executing the program.

For example, an arbitrary computer such as a PC is capable of realizing the control apparatus 80. As a matter of course, hardware such as an FPGA and an ASIC may be used.

In the present embodiment, a control unit as a functional block is configured by the CPU executing a predetermined program. As a matter of course, dedicated hardware such as an integrated circuit (IC) may be used in order to realize the functional blocks.

The program is installed to the control apparatus 80 via various recording media for example. Alternatively, the program may be installed via the Internet or the like.

The type of recording medium for recording the program and the like are not limited, and an arbitrary computer-readable recording medium may be used. For example, a computer-readable non-transitory arbitrary storage medium may be used.

As shown in FIG. 5, the control apparatus 80 has an image acquisition unit 81, a recognition unit 82, a control unit 83, and a graphical user interface (GUI) presentation unit 84.

The image acquisition unit 81 acquires a captured image of the patient eyeball. In the present embodiment, the image acquisition unit 81 acquires a front image and a tomographic image from the front image capturing unit 63 and the tomographic image capturing unit 64 of the surgical microscope 21.

The acquired front image and tomographic image are output to the recognition unit 82 and the display unit 91 of the phaco machine 90.

The recognition unit 82 recognizes the situation information relating to the surgery on the basis of the captured image relating to the patient eyeball. In the present embodiment, a currently performed phase of the surgery is recognized on the basis of the front image and the tomographic image. The phase of the surgery is recognized for example on the basis of a surgical instrument in the front image, such as a scalpel and a fragmentation unit (e.g., on the basis of the type of surgical instrument used). Moreover, whether or not a situation where the surgical instrument can damage the posterior capsule or the retina (dangerous situation) is recognized for example on the basis of the tomographic image.

The dangerous situation is a dangerous situation relating to the surgery. For example, the dangerous situation can be a situation where the posterior capsule is subjected to aspiration (the posterior capsule can be damaged). In a case where the posterior capsule is damaged, it corresponds to a situation where the recognition unit 82 does not recognize the cortex from the captured image acquired by the image acquisition unit 81.

Moreover, in the present embodiment, the recognition unit 82 recognizes situation information of the captured image or a dangerous situation on the basis of a learned model obtained by performing learning about the situation information and the dangerous situation. A specific example will be described later.

It should be noted that a method of recognizing the situation information and the dangerous situation is not limited. For example, the captured image may be analyzed by machine learning. Alternatively, image recognition, semantic segmentation, image signal analysis, and the like may be used.

The recognized situation information and dangerous situation are output to the control unit 83 and the GUI presentation unit 84.

In the present embodiment, in the cataract surgery, the learned model is a classifier generated by performing learning using data in which the phases of the "aspiration through the surgical instrument distal end" and the "fragmentation of the lens nucleus" are associated with the parameter relating to the ultrasonic output, the parameter relating to aspiration through the surgical instrument distal end, and the parameter relating to the inflow of the perfusion solution in the phase as learning data.

It should be noted that a method of learning a learning model for obtaining the learned model is not limited. For example, any machine learning algorithm using a deep neural network (DNN) or the like may be used. For example, artificial intelligence (AI) or the like that performs deep learning may be used.

For example, the above-mentioned recognition unit performs image recognition. A learned model performs machine learning on the basis of input information and outputs a recognition result. Moreover, the recognition unit performs recognition of the input information on the basis of the recognition result of the learned model.

For example, neural network and deep learning are used for learning techniques. The neural network is a model that mimics neural networks of a human brain. The neural network is constituted by three types of layers of an input layer, an intermediate layer (hidden layer), and an output layer.

The deep learning is a model using neural networks with a multi-layer structure. The deep learning can repeat characteristic learning in each layer and learn complicated patterns hidden in mass data.

The deep learning is, for example, used for the purpose of identifying objects in a captured image. For example, a convolutional neural network (CNN) or the like used for recognition of an image or moving image is used.

Moreover, a neuro chip/neuromorphic chip in which the concept of the neural network has been incorporated can be used as a hardware structure that realizes such machine learning.

In the present embodiment, a suitable control parameter in the phase is output to the control unit 83 on the basis of the learned model incorporated in the recognition unit 82.

Now, a specific example of the learned model will be described below.

Specific Example 1: the input data is a "captured image" and the training data is "phases 1 to 5 of fragmentation of the lens nucleus".

In Specific Example 1, situation information of the captured image is added to each input captured image. That is, learning using data obtained by applying the situation information to each captured image as learning data is performed, and a learned model is generated. For example, information indicating that the phase is the fragmentation 2 of the lens nucleus is added to a captured image in which the residual amount of the nucleus of the lens is 80%. Moreover, for example, in a case where the residual amount of the nucleus of the lens is 20%, information indicating that the phase is the fragmentation 5 of the lens nucleus is added. That is, detailed phases of the phase are determined referencing the residual amount of the nucleus of the lens. Moreover, which phase corresponds to the captured image is annotated by a person concerned with ophthalmology, such as a surgeon (ophthalmologist). It should be noted that an arbitrary phase may be set with respect to the residual amount of the nucleus of the lens. As a matter of course, it is not limited to the five phases.

Based on such a learned model, the recognition unit 82 is capable of recognizing each phase of the captured image.

It should be noted that the captured image input in Specific Example 1 may be an image obtained by imaging only the cornea portion of the patient eyeball. Accordingly, the precision can be enhanced by excluding unnecessary learning data for learning.

It should be noted that a portion corresponding to the cornea portion of the input captured image may be cut out.

Specific Example 2: the input data is a "captured image" and the training data is "phases 1 to 5 of cortex aspiration".

In Specific Example 2, situation information of the captured image is added by the user to each input captured image. For example, information indicating that the phase is cortex aspiration 5 is added to the captured image in which the residual amount of the cortex is 20%. Moreover, which phase corresponds to the captured image is annotated by a person concerned with ophthalmology, such as a surgeon.

The recognition unit 82 is capable of recognizing each phase of the captured image on the basis of the above-mentioned learned model.

It should be noted that the captured image input in Specific Example 2 may be an image obtained by imaging only the cornea portion of the patient eyeball.

Specific Example 3: the input data is a "captured image" and the training data is "whether or not cortex aspiration occurs" or the input data is a "captured image and a sensing result of a sensor (sensor unit 96 to be described later) mounted on the treatment apparatus" and the training data is "whether or not posterior capsule aspiration occurs".

In a first learning method in Specific Example 3, training data indicating that "cortex aspiration occurs" is added in a case where there is a cortex at the surgical instrument distal end in the captured image or training data indicating that "cortex aspiration does not occur" in a case where there is no cortex at the surgical instrument distal end, and learning for determining whether or not cortex aspiration occurs on the basis of the captured image is performed. Based on a result of the learning, the recognition unit 82 determines whether or not cortex aspiration occurs through the captured image. Then, in a case where a reduction in amount of aspiration is found as a sensing result of the sensor when it is determined that "cortex aspiration does not occur", it is recognized that the posterior capsule is aspirated at the surgical instrument distal end (though it is not easy to make a determination on the basis of the captured image).

In a second learning method in Specific Example 3, a "captured image and a sensing result of the sensor (sensor unit 96 to be described later) mounted on the treatment apparatus" are added as the input data and whether or not posterior capsule aspiration has occurred actually is added as the training data to each piece of input data. Based on this learning result, the recognition unit 82 recognizes whether or not posterior capsule aspiration occurs directly on the basis of the "captured image and the sensing result of the sensor (sensor unit 96 to be described later) mounted on the treatment apparatus".

It should be noted that in this case, the captured image and the sensing result when the posterior capsule is aspirated are required as the input data. At that time, a captured image in which the posterior capsule is aspirated actually during surgery may be used or an image that reproduces virtually a status in which the posterior capsule is aspirated may be used for learning.

It should be noted that the captured image input in Specific Example 3 may be an image obtained by imaging only the cornea portion of the patient eyeball.

The control unit 83 controls a control parameter on the basis of the situation information. In the present embodiment, the control parameter is controlled in accordance with the phase recognized by the recognition unit 82.

For example, in the cataract surgery, the phase (first phase) where a predetermined amount or more of the nucleus of the lens remains is recognized in image recognition by the recognition unit 82. In this phase, in order to remove the nucleus of the lens quickly, the control unit 83 sets a maximum value of an ultrasonic wave that can be output in the first phase to be a maximum output value of the phaco machine 90, for example. Moreover, in the phase where a predetermined amount or less of the nucleus of the lens remains, in order to prevent a dangerous situation where the posterior capsule is damaged, the maximum value of the ultrasonic wave that can be output is set to be a limited value (lower value) than the maximum value of the ultrasonic wave that can be output in the first phase.

Figure 6A:
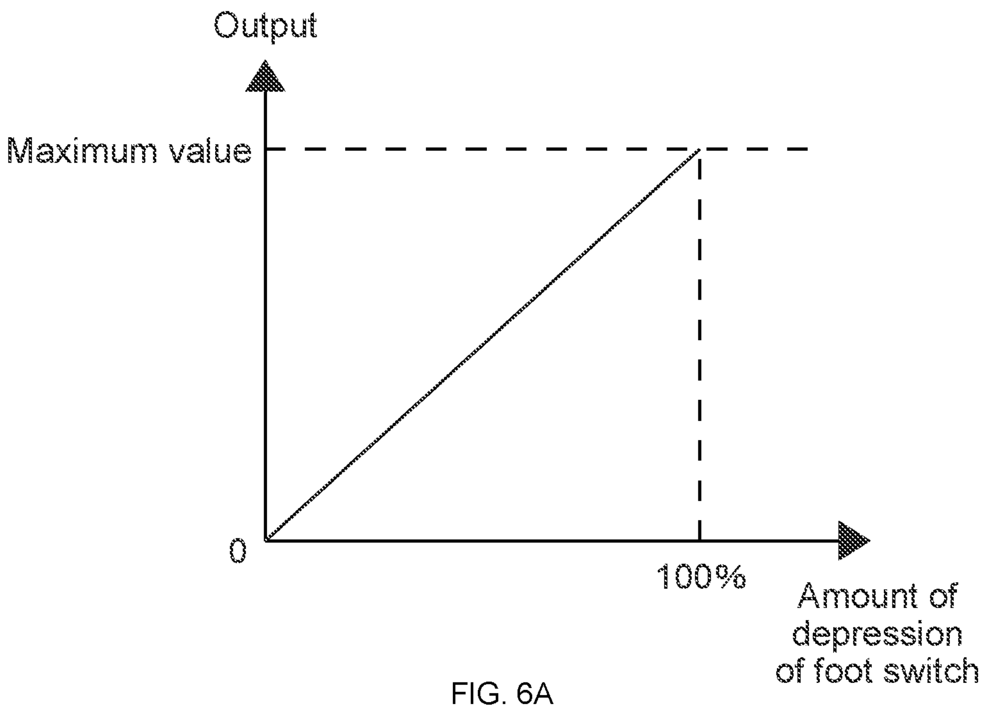
FIGS. 6A and 6B The graphs showing a basic control example of a control parameter.
Figure 6B:
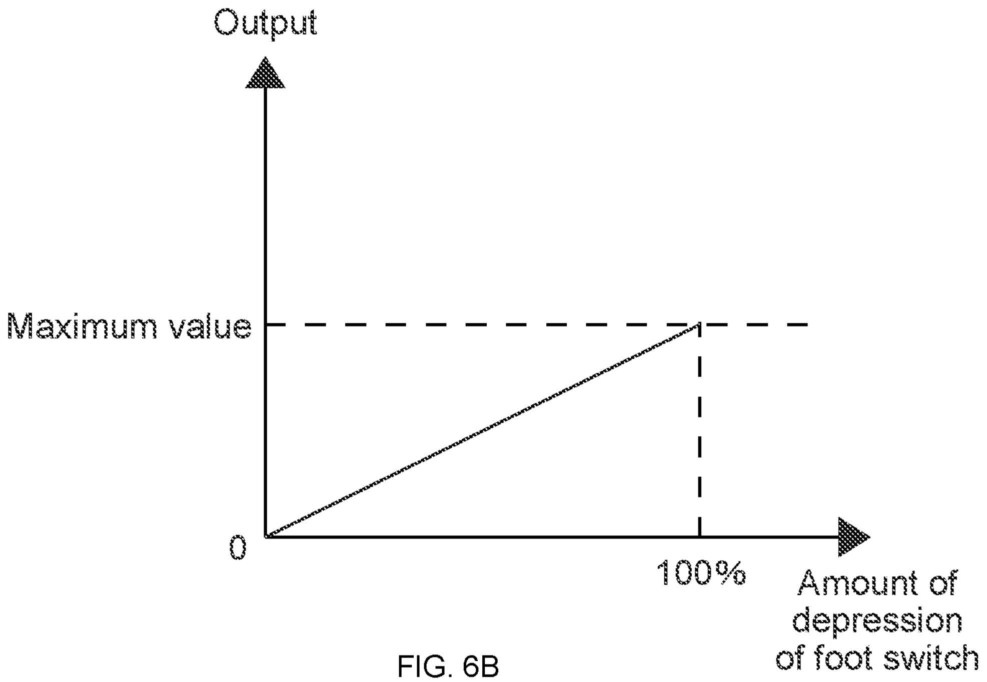

Now, a basic control example will be described with reference to FIGS. 6A and 6B. FIGS. 6A and 6B are graphs showing a basic control example of the control parameter. As shown in FIGS. 6A and 6B, the vertical axis indicates the output of the control parameter and the horizontal axis indicates the amount of depression of the foot switch. Moreover, in FIGS. 6A and 6B, the phase of the "fragmentation of the lens nucleus" is taken as an example. That is, the vertical axis indicates the ultrasonic output.

FIG. 6A is a graph showing a control example in the fragmentation 1 of the lens nucleus.

As shown in FIG. 6A, the user is able to output an ultrasonic wave up to the maximum value by depressing the foot switch 93 up to the maximum (100%). In FIG. 6A, because of a phase where a sufficient amount of the lens nucleus remains, the maximum value of the ultrasonic wave can be output up to a high numerical value, for example, a maximum output value (100%) of the phaco machine 90 by the user depressing the foot switch 93. As a matter of course, the ultrasonic wave to be output is not constantly 100% and the value of the ultrasonic wave to be output is arbitrarily changed in accordance with a user operation (an amount of depression of the foot switch 93).

FIG. 6B is a graph showing a control example in the fragmentation 4 of the lens nucleus.

As shown in FIG. 6B, because of a status in which the residual amount of the lens nucleus is small, the maximum value of the ultrasonic output is controlled. For example, in order not to damage the posterior capsule and the like, the maximum value of the ultrasonic wave is controlled to be a value (e.g., 30%) lower than the maximum output value of the phaco machine 90.

Moreover, since the maximum value of the ultrasonic output is reduced, the gradient of the straight line (solid line) shown in FIG. 6B is gentler than the gradient of the straight line (solid line) shown in FIG. 6A. That is, a variation in value of the ultrasonic output, which depends on the amount of depression of the foot switch 93, decreases. Accordingly, more specific, accurate output control can be made.

It should be noted that the control method is not limited, and the maximum value of the output of the control parameter in each phase may be arbitrarily set. Moreover, the amount of depression of the foot switch 93 may be controlled. For example, when depressing the foot switch 93 at the maximum, a control parameter corresponding to 50% of the amount of depression may be output.

Moreover, information indicating that the maximum output value of the phaco machine 90 is controlled may be displayed on the display unit 91. For example, information indicating that the current maximum value of the ultrasonic wave that can be output is 30% of the maximum output value of the phaco machine 90 is displayed on the display unit 91.

The GUI presentation unit 84 presents various types of information relating to the surgery to the user. In the present embodiment, the GUI presentation unit 84 presents a GUI that enables the user to visually recognize the current situation information, the controlled control parameter, and the dangerous situation on the display unit 91 of the phaco machine 90 or the monitor 34 of the surgical microscope 21.

As shown in FIG. 5, the phaco machine 90 has the sensor unit 96 and a bottle adjustment unit 97 as well as the display unit 91, the fragmentation unit 92, the foot switch 93, and the bottle 94. In the present embodiment, the control unit 83 controls the output of the ultrasonic wave output from the fragmentation unit 92, the pressure of aspiration or the amount of aspiration of the fragmentation unit 92, the height of the bottle 94 (inflow pressure of the perfusion solution), and the like.

The sensor unit 96 is a sensor device mounted on the fragmentation unit 92. For example, the sensor unit 96 is a pressure sensor and measures a pressure of aspiration of the fragmentation unit 92 that aspirates the waste. The sensing result measured by the sensor unit 96 is supplied to the control unit 83. Moreover, the sensing result measured by the sensor unit 96 may be displayed on the display unit 91.

The bottle adjustment unit 97 is a drive mechanism capable of adjusting the height of the bottle 94. For example, when increasing the inflow of the perfusion solution, the height of the bottle 94 is adjusted to be high.

It should be noted that in the present embodiment, the recognition unit 82 corresponds to a recognition unit that recognizes the situation information relating to the surgery on the basis of the captured image relating to the patient eyeball captured by the surgical microscope.

It should be noted that in the present embodiment, the control unit 83 corresponds to a control unit that controls the control parameter relating to the treatment apparatus used for the above-mentioned surgery on the basis of the situation information.

It should be noted that in the present embodiment, the GUI presentation unit 84 corresponds to a presentation unit that presents at least one of the situation information or the control parameter to a user who performs the surgery.

It should be noted that in the present embodiment, the phaco machine 90 corresponds to a treatment apparatus used for cataract surgery.

It should be noted that in the present embodiment, the surgical system 11 corresponds to an ophthalmic surgical system including a surgical microscope capable of capturing an image of a patient eyeball, a treatment apparatus used for surgery of the patient eyeball, and a control apparatus including a recognition unit that recognizes situation information relating to the surgery on the basis of a captured image relating to the patient eyeball and a control unit that controls a control parameter relating to the treatment apparatus on the basis of the situation information.

Figure 7A:
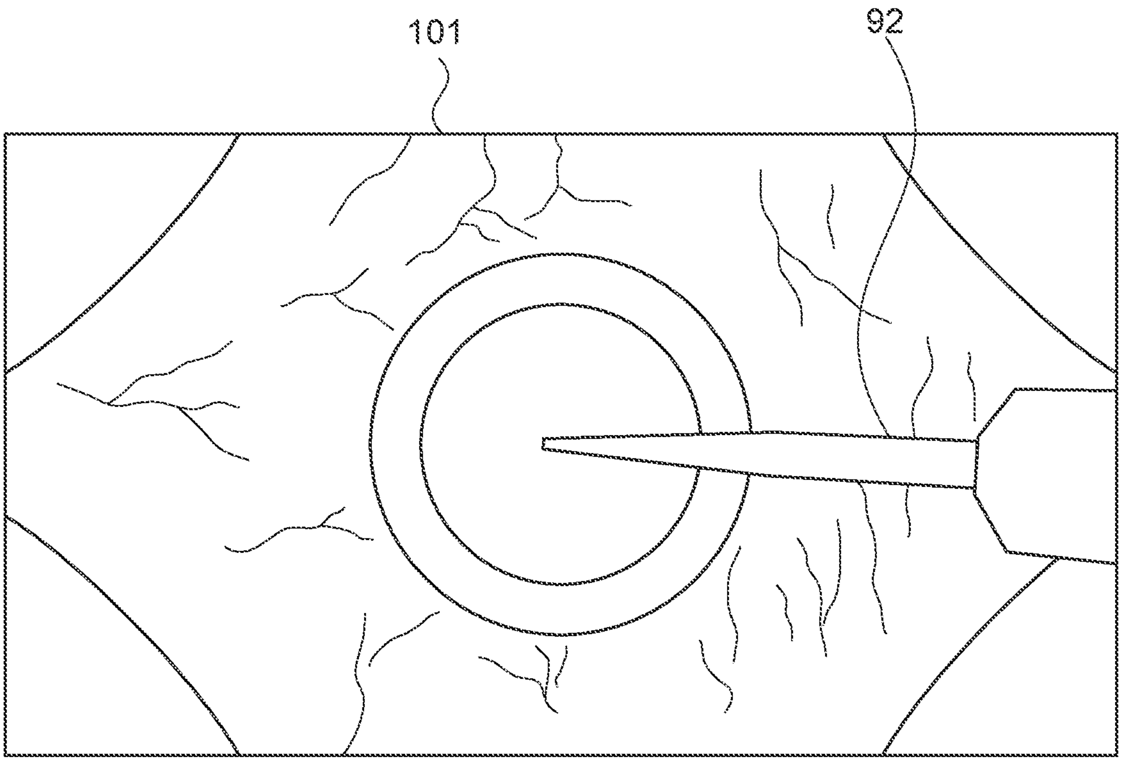
FIGS. 7A and 7B The schematic diagrams showing image recognition in each phase and a control example of the control parameter.
Figure 7B:
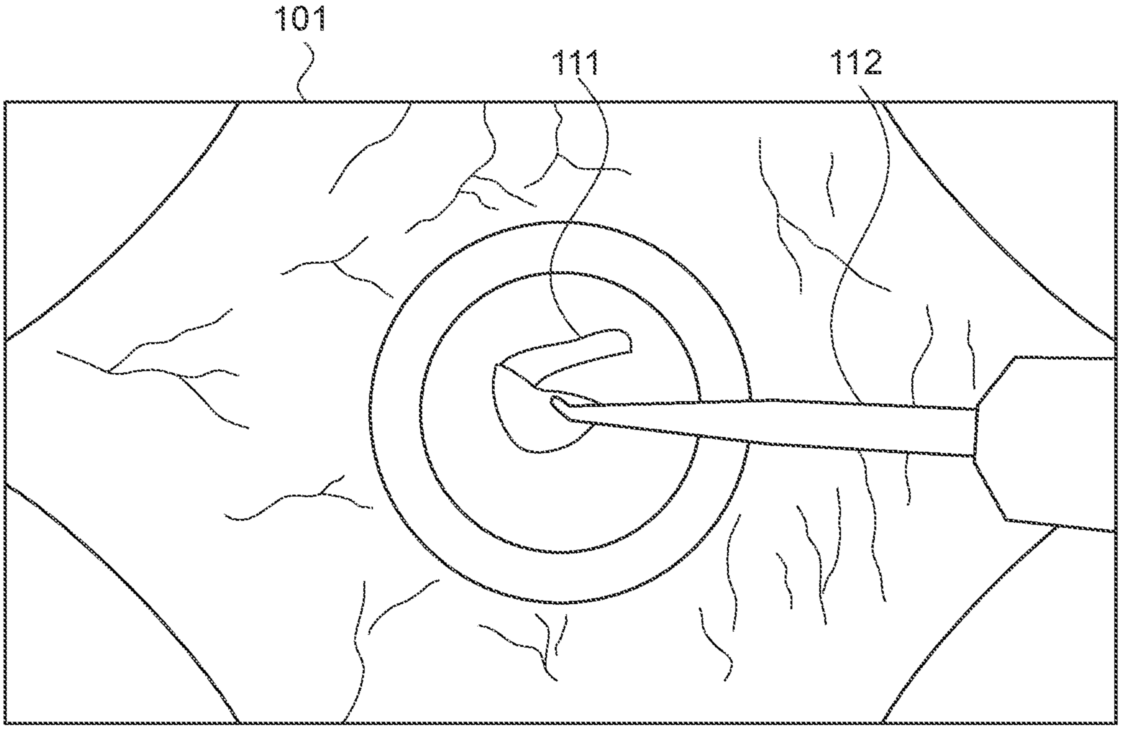

FIGS. 7A and 7B are schematic diagrams showing the image recognition in each phase and a control example of the control parameter.

FIG. 7A is a schematic diagram showing the phase of the fragmentation of the lens nucleus.

As shown in FIG. 7A, the recognition unit 82 recognizes that the current phase is the “fragmentation of the lens nucleus” on the basis of the surgical instrument (fragmentation unit 92) in the captured image.

On the basis of the recognition result by the recognition unit 82, the control unit 83 controls the output of the ultrasonic wave output to the fragmentation unit 92 to be the maximum output value of the phaco machine 90.

For example, in a case where it is recognized that the residual amount of the nucleus of the lens of the patient eyeball 101 is large on the basis of the image recognition by the recognition unit 82, the maximum value of the output of the ultrasonic wave output from the fragmentation unit 92 is controlled to be the maximum output value of the phaco machine 90. Moreover, for example, in a case where it is recognized that the nucleus of the lens of the patient eyeball 101 is little as a result of image recognition by the recognition unit 82, i.e., in the phase (second phase) where a predetermined amount or less of the nucleus of the lens remains, the maximum value of the output of the ultrasonic wave output from the fragmentation unit 92 is set to be a value lower than the maximum value of the ultrasonic wave that can be output in the first phase.

It should be noted that a method of limiting the ultrasonic output is not limited. For example, a variation in ultrasonic output may be reduced. That is, a variation in ultrasonic output may be controlled to be smaller with respect to the amount of depression of the foot switch 93. Moreover, the maximum value of the ultrasonic output to be limited may be controlled to be an optimal value by the machine learning or the user.

FIG. 7B is a schematic diagram showing the phase of the aspiration through the surgical instrument distal end.

As shown in FIG. 7B, the recognition unit 82 recognizes that the current phase is the “aspiration through the surgical instrument distal end” on the basis of the surgical instrument in the captured image (e.g., an aspiration unit 112 that aspirates a cortex 111). It should be noted that in FIG. 7B, the aspiration unit 112 is aspirating the cortex 111.

The control unit 83 controls the pressure of aspiration or the amount of aspiration of the aspiration unit 112 on the basis of the recognition result by the recognition unit 82. For example, in a case where a sufficient amount of the cortex 111 remains, the maximum value of the pressure of aspiration or the amount of aspiration of the aspiration unit 112 is controlled to be the maximum output value of the phaco machine 90.

Moreover, in a case where the cortex 111 is not recognized in the image recognition by the recognition unit 82, the control unit 83 lowers the pressure of aspiration or the amount of aspiration of the aspiration unit 112 because the posterior capsule can be aspirated.

It should be noted that the recognition unit 82 may recognize whether or not the cortex 111 is sufficiently aspirated on the basis of the pressure of aspiration and the amount of aspiration of the aspiration unit 112, which is measured by the sensor unit 96.

Hereinabove, in the control apparatus 80 according to the present embodiment, the situation information relating to the surgery is recognized on the basis of the captured image relating to the patient eyeball 101, which is captured by the surgical microscope 21. The control parameter relating to the phaco machine 90, which is used for the cataract surgery, is controlled on the basis of the situation information. Accordingly, precise control can be made efficiently.

Conventionally, in the cataract surgery, the lens nucleus is removed by the phacoemulsification. Moreover, there is a case where it is desirable to perform the ultrasonic output finely, for example, there is a case where it is desirable to remove the lens nucleus quickly or there is a case where it is desirable to make an operation without damaging the posterior capsule and the like. However, the ultrasonic output uniquely corresponds to a degree of depressing the foot switch. Therefore, fine control is difficult.

In view of this, in the present technology, the phase of the surgery is recognized by image recognition, and control is made in accordance with the phase. Accordingly, precise and fine output control can be made efficiently in accordance with a situation. Moreover, the precision of predicting the dangerous situation is enhanced by determining a situation of the surgery from an image by machine learning.

Second Embodiment

A control apparatus according to a second embodiment of the present technology will be described. Hereinafter, descriptions of portions having those similar to the configurations and actions of the surgical microscope 21, the control apparatus 80, and the like described in the embodiment above will be omitted or simplified.

In the above-mentioned embodiment, the surgical system 11 includes the phaco machine 90. The present technology is not limited thereto, and various types of treatment apparatuses related to eyeball surgery may be used instead of the phaco machine 90. Hereinafter, a specific description of vitreous removal will be given.

In the above-mentioned embodiment, the control parameter is controlled in accordance with the phase of the cataract surgery. The present technology is not limited thereto, and the control parameter may be controlled in accordance with a phase of the vitreous removal.

In a case of the vitreous removal, it is divided into the following phases.

Eyeball incision: a phase where a hole through which a surgical instrument for removing the vitreous can be inserted is made in a patient eyeball. Typically, three holes are made for inserting a vitreous cutter for removing the vitreous, an optical fiber that irradiates the inside of the eyeball with light, and an instrument that causes perfusion solution to flow in.

Surgical instrument insertion: a phase where the surgical instruments are inserted into the made holes.

Vitreous removal: a phase where the vitreous is removed by the vitreous cutter. In the present embodiment, it is divided into a phase where a distance between a position of a posterior capsule or retina and a position of the vitreous cutter is equal to or longer than a predetermined distance and a phase where the distance between the position of the posterior capsule or retina and the position of the vitreous cutter is equal to or shorter than the predetermined distance.

Laser irradiation: a phase where an affected part such as a retinal tear is irradiated with a laser by a laser probe.

In the above-mentioned embodiment, the control parameter includes at least one of the parameter relating to the ultrasonic output, the parameter relating to aspiration through the surgical instrument distal end, or the parameter relating to the inflow of the perfusion solution. The present technology is not limited thereto, and the control parameter may include an arbitrary parameter relating to the surgery. In the second embodiment, the control parameter includes at least one of the parameter relating to the speed of the vitreous removal or the parameter relating to the laser output.

The parameter relating to the speed of the vitreous removal is a parameter indicating a speed of the vitreous cutter in removing the vitreous. For example, the parameter is the number of reciprocations per second (cut rate) of a blade of the vitreous cutter.

The parameter relating to the laser output is a parameter indicating the output of the laser output from the laser probe. In the present embodiment, control of the parameter relating to the laser output includes laser intensity and prohibition of laser emission.

In the above-mentioned embodiment, the control parameter is controlled on the basis of the situation information and the dangerous situation in the cataract surgery. The present technology is not limited thereto, and the control parameter may be controlled on the basis of the situation information and the dangerous situation in the vitreous removal.

For example, the dangerous situation in the vitreous removal includes a situation where a laser for the vitreous removal can be emitted to a macula.

Moreover, for example, in a case of the vitreous removal, a phase where the distance between the position of the posterior capsule or retina and the position of the vitreous cutter is equal to or longer than the predetermined distance is recognized in the image recognition by the recognition unit 82. In this phase, the control unit 83 increases the cut rate in order to remove the vitreous quickly. Moreover, in a phase where the distance between the position of the posterior capsule or retina and the position of the vitreous cutter is equal to or shorter than the predetermined distance, the posterior capsule or the retina can be damaged. Therefore, the cut rate or the maximum value of the parameter relating to the aspiration through the surgical instrument distal end is controlled to lower.

Moreover, the control unit 83 controls the control parameter on the basis of the dangerous situation. For example, in a case where the distance between the retina and the vitreous cutter is close according to the recognition unit 82, the cut rate is controlled to lower. Moreover, for example, in a case where an aiming beam approaches to fall within a predetermined distance from the macula, the laser irradiation is prohibited.

In the above-mentioned embodiment, the recognition unit 82 recognizes each phase on the basis of the learned model shown in Specific Examples 1 to 3. Alternatively, various types of machine learning may be performed.

Now, other specific examples of the learned model will be described.

Specific Example 4: the input data is a "captured image" and the training data is a "position of the surgical instrument distal end".

In Specific Example 4, a position of the surgical instrument distal end is detected from the input captured image. That is, a detection result of the position of the surgical instrument distal end is learned with respect to the input captured image. For example, the position of the surgical instrument distal end is learned by segmentation or the like.

Based on such a learned model, the recognition unit 82 is capable of recognizing a position of the surgical instrument distal end in a captured image.

Moreover, a distance between the surgical instrument and the retina is estimated from the captured image on the basis of the position of the surgical instrument and depth information, the depth information being based on a front position of the retina in the captured image and a parallax.

Moreover, the phase is set on the basis of a mean value of distances between the surgical instrument and the retina, which are estimated within a certain time.

It should be noted that more detailed phases of the phase may be set by threshold processing. Moreover, the maximum value of the control parameter may be determined on the basis of the mean value of the distances.

Specific Example 5: the input data is a "captured image" and the training data is "a position of the surgical instrument distal end, an orientation, a position of the aiming beam, or a site of the eye".

In Specific Example 5, a position of the surgical instrument distal end, an orientation, a position of the aiming beam, or a site of the eye is detected from the input captured image. For example, two points in an input captured image, i.e., a point showing the surgical instrument distal end and a range in which the orientation of the surgical instrument distal end can be seen, for example, a point showing a distance of 1 mm are learned. Moreover, a position of the aiming beam, an anterior segment of the eyeball, a posterior segment of the eyeball, the macula, an optic disc, or the like is learned by semantic segmentation, for example.

That is, on the basis of the above-mentioned learned model, the recognition unit 82 is capable of recognizing a position of the surgical instrument distal end, an orientation, a position of the aiming beam, or a site of the eye from a captured images.

It should be noted that the number of points used for learning is not limited, and only one point showing the surgical instrument distal end may be used.

Moreover, the control unit 83 controls the following two modes by the above-mentioned learning. The first mode is a mode of prohibiting the laser emission in a case where it is detected from the captured image that the aiming beam overlaps the site (macula or optic disc) of the eyeball. The second mode is a mode of prohibiting the laser emission in a case where it is detected from the captured image that the site of the eye is located within a certain distance in the captured image from the surgical instrument distal end such as the laser probe in the orientation of the surgical instrument.

Figure 8:
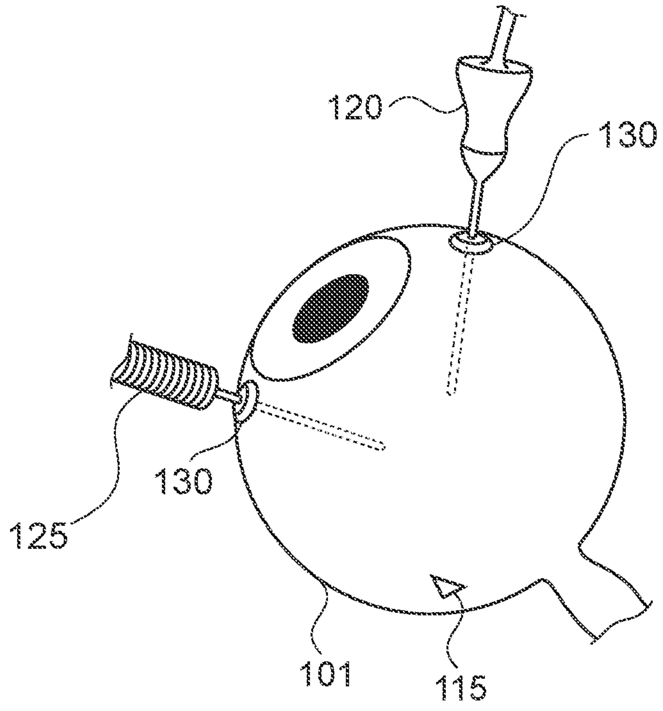
FIG. 8 A schematic diagram showing a status of vitreous removal.

FIG. 8 is a schematic diagram showing a status of the vitreous removal.

As shown in FIG. 8, a surgical instrument 120 and an intraocular illumination device 125 are inserted into a patient eyeball 101 with a hole 115 in the retina (not shown). It should be noted that a pipe for causing perfusion solution to flow in is not shown in FIG. 8. Moreover, in FIG. 8, tubular trocars 130 serving to guide the surgical instrument 120 or the intraocular illumination device 125 in inserting or removing the surgical instrument 120 or the intraocular illumination device 125 are placed on the patient eyeball 101.

A surgical instrument depending on each phase of the vitreous removal is used as the surgical instrument 120. In the present embodiment, phases ("vitreous removal" and "laser irradiation") where the vitreous cutter and the laser probe are each inserted as the surgical instrument 120 are focused. As a matter of course, forceps, a back flash needle, internal limiting membrane (ILM) forceps, and the like may be inserted.

The intraocular illumination device 125 lights up the inside of the patient eyeball 101 with light. For example, the intraocular illumination device 125 has an illumination light source and an optical fiber. The illumination light source emits, for example, illumination light for emitting light to the inside of the patient eyeball 101 for vitrectomy surgery or the like that requires wide-area observation of an ocular fundus. The optical fiber guides the illumination light emitted from the illumination light source and emits the illumination light to the inside of the patient eyeball 101.

Figure 9:
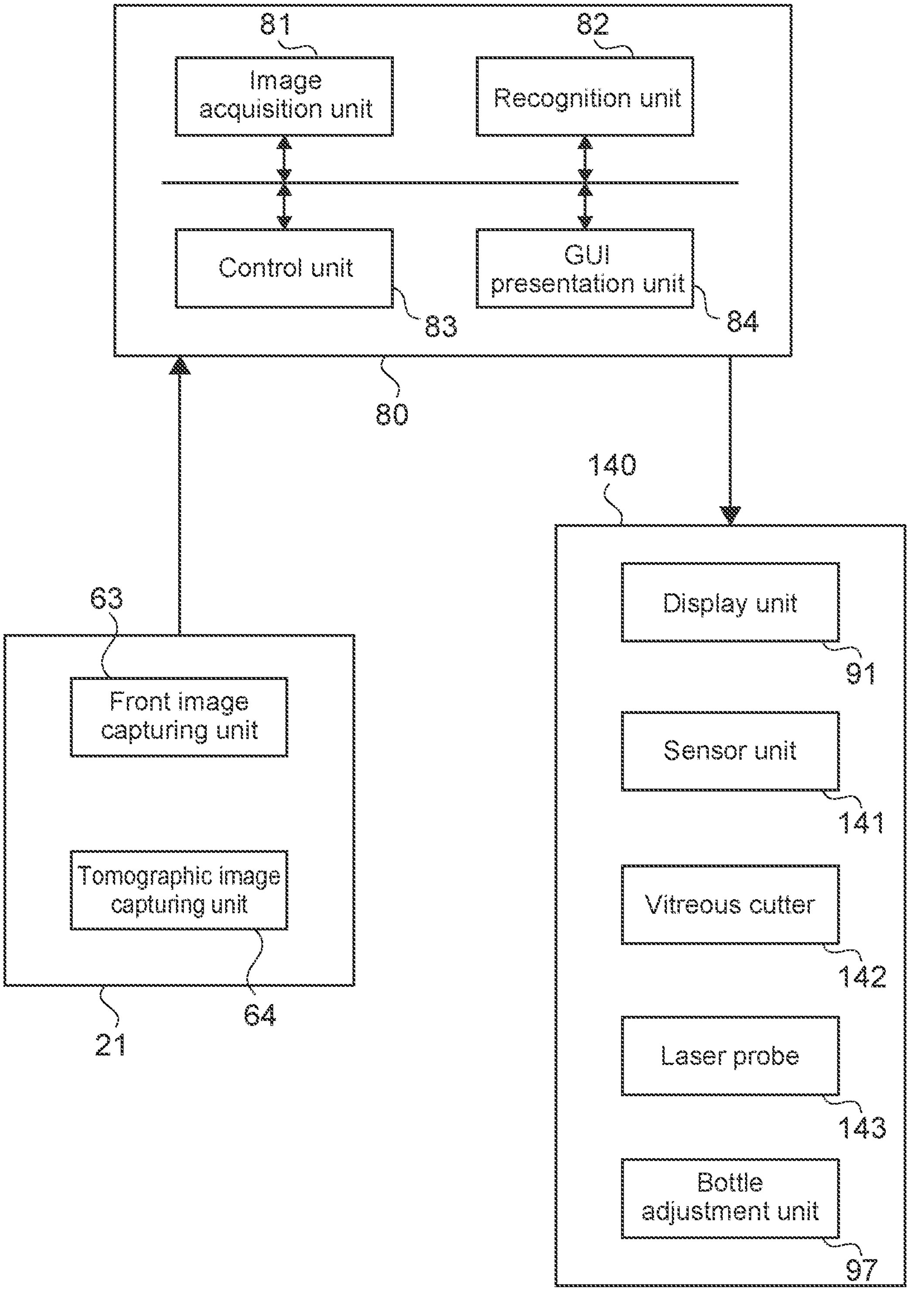
FIG. 9 A block diagram schematically showing another functional configuration example of the surgical system.

FIG. 9 is a block diagram schematically showing another functional configuration example of the surgical system 11. As shown in FIG. 9, the surgical system 11 has the surgical microscope 21, the control apparatus 80, and a vitrectomy apparatus 140.

The surgical microscope 21, the control apparatus 80, and the vitrectomy apparatus 140 are connected to be capable of communicating with each other with a wire or wirelessly. A connection form between the devices is not limited, and for example, can use wireless LAN communication such as Wi-Fi or near-field communication such as Bluetooth (registered trademark).

The vitrectomy apparatus 140 is a treatment apparatus used for the vitreous removal and an arbitrary configuration is provided. For example, the vitrectomy apparatus 140 has a display unit 91, a sensor unit 141, a vitreous cutter 142, a laser probe 143, and a bottle adjustment unit 97 as main components in FIG. 8. It should be noted that the display unit 91 and the bottle adjustment unit 97 have the same configurations as the phaco machine 90, and therefore descriptions thereof will be omitted.

It should be noted that in the present embodiment, the vitrectomy apparatus 140 corresponds to a treatment apparatus used for vitrectomy surgery.

The vitreous cutter 142 is capable of removing and aspirating the vitreous of the patient eyeball 101. In the present embodiment, the control unit 83 of the control apparatus 80 controls the cut rate of the vitreous cutter 142 and the pressure of aspiration or the amount of aspiration. Moreover, the vitreous cutter 142 is provided with the sensor unit 141 and measures the amount of aspiration or the pressure of aspiration in aspirating through the surgical instrument distal end.

For example, in the phase of the "vitreous removal", in a case where a distance between a position of the posterior capsule or retina and a position of the vitreous cutter 142 is equal to or longer than a predetermined distance, the control unit 83 controls the parameter relating to the speed of the vitreous removal to be a maximum value of a cut rate of the vitreous cutter 142. Moreover, for example, in a case where the distance between the position of the posterior capsule or retina and the position of the vitreous cutter 142 is equal to or shorter than the predetermined distance, the control unit 83 decreases the maximum value of the cut rate of the vitreous cutter 142 of the parameter relating to the speed of the vitreous removal.

The laser probe 143 irradiates an affected part such as a retinal tear with a laser. For example, the laser probe 143 is capable of emitting a particular-wavelength laser to the retina, thereby coagulating the retina. Moreover, the laser probe 143 radiates an aiming beam showing a position to which the laser is emitted. The user is able to check a position to which the laser is emitted on the basis of the position of the aiming beam from the captured image.

In the present embodiment, the control unit 83 controls laser emission of the laser probe 143. For example, in a case where the recognition unit 82 recognizes that an aiming beam approaches to fall within a predetermined distance from the macula, the control unit 83 prohibits the laser emission.

Figure 10A:
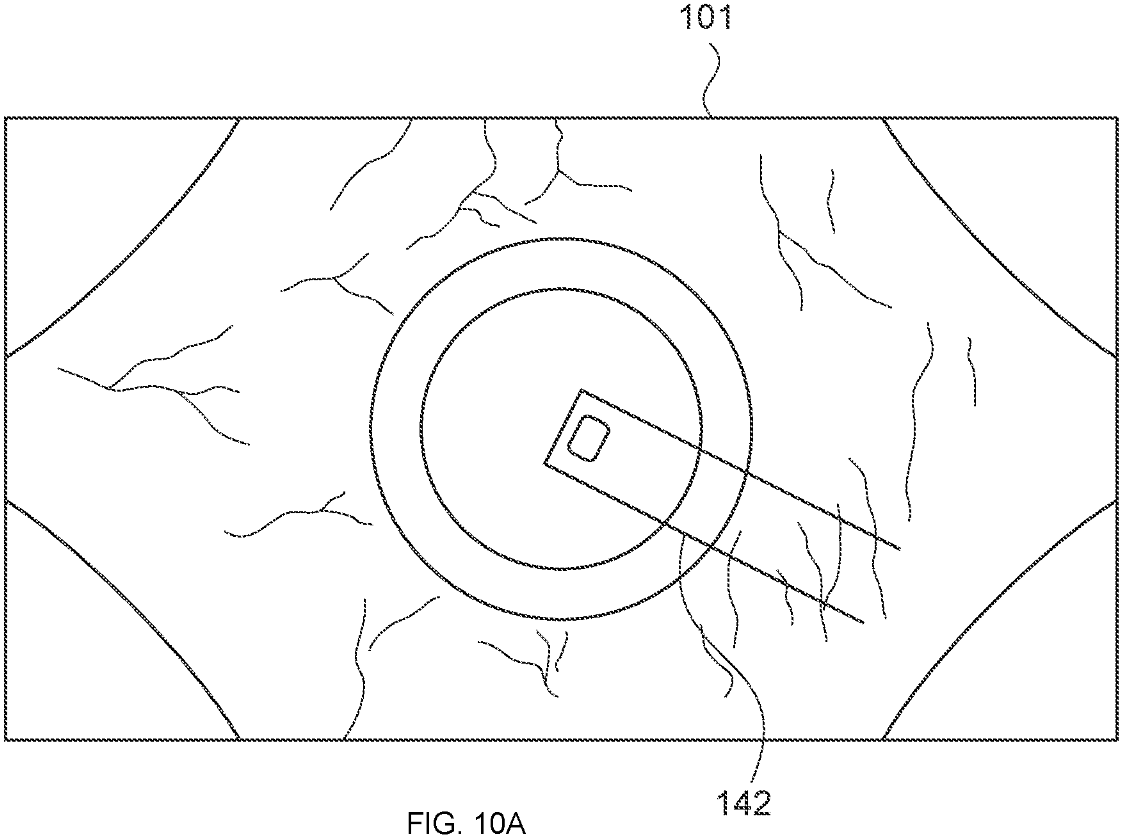
FIGS. 10A and 10B The schematic diagrams showing image recognition in each phase and a control example of the control parameter.
Figure 10B:
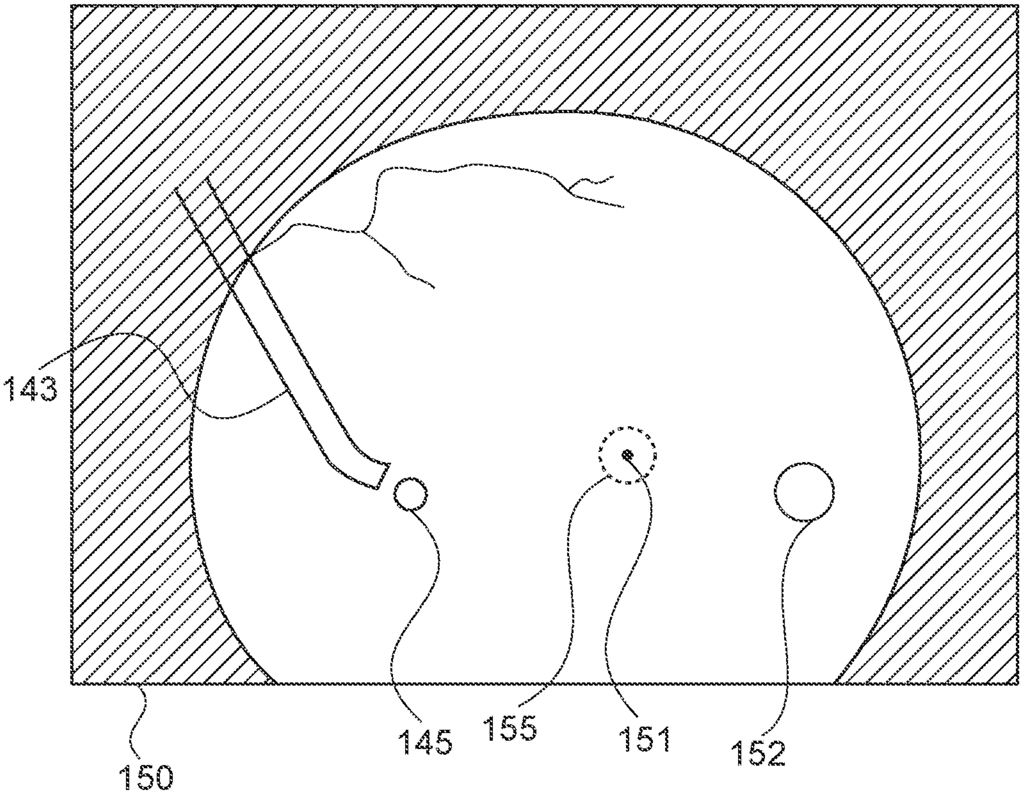

FIGS. 10A and 10B are schematic diagrams showing the image recognition in each phase and a control example of the control parameter.

FIG. 10A is a schematic diagram showing the phase of the vitreous removal.

As shown in FIG. 10A, the recognition unit 82 recognizes that the current phase is the "vitreous removal" on the basis of the surgical instrument (vitreous cutter 142) in the captured image.

The control unit 83 controls the cut rate of the vitreous cutter 142 on the basis of the recognition result by the recognition unit 82. In a case where the distance between the position of the posterior capsule or retina and the position of the vitreous cutter 142 is equal to or longer than the predetermined distance, the maximum value of the cut rate is increased. For example, the maximum value of the cut rate is set to be the maximum output value of the vitrectomy apparatus 140.

In a case where the distance between the position of the posterior capsule or retina and the position of the vitreous cutter 142 is equal to or shorter than the predetermined distance, the maximum value of the cut rate is decreased. For example, the maximum value of the cut rate is controlled to be a value lower than the maximum output value of the vitrectomy apparatus 140.

It should be noted that a control method for the cut rate is not limited. For example, a variation in cut rate may be decreased. Moreover, for example, the maximum value of the cut rate to be limited may be controlled to be an optimal value by machine learning or the user. Moreover, the maximum value may be controlled to lower in accordance with, for example, an elapse time from a time when the phase of the "vitreous removal" is started.

FIG. 10B is a schematic diagram showing the phase of the laser irradiation.

As shown in FIG. 10B, the image acquisition unit 81 acquires a captured image 150 obtained by capturing an image of a laser probe 143, an aiming beam 145, a macula 151, and an optic disc 152.

The recognition unit 82 recognizes that the current phase is the "laser irradiation" on the basis of the surgical instrument (laser probe 143) in the captured image.

The control unit 83 prohibits the laser emission of the laser probe 143 in a case where the aiming beam 145 comes within a predetermined distance (dotted line 155) from the macula 151.

The control unit 83 may prohibit the laser emission of the laser probe 143 in a case where the aiming beam 145 comes within the predetermined distance from the optic disc 152. In this case, the dotted line 155 that is the basis is set to be in the periphery of the optic disc.

Moreover, the GUI presentation unit 84 outputs to the display unit 91 such a GUI that the user can visually recognize the dotted line 155. The dotted line 155 may be changed in color (e.g., changed to red from green) before and after the aiming beam 145 enters the inside of the dotted line 155. Accordingly, the user can know that the aiming beam 145 enters the emission-prohibited region. Moreover, the GUI with which the dotted line 155 can be visually recognized may be just presented without prohibiting the laser emission. Accordingly, the risk that the user may emit a laser to the macula 151 or the optic disc 152 is lowered.

Other Embodiments

The present technology is not limited to the above-mentioned embodiments, and various other embodiments can be realized.

In the above-mentioned embodiments, the control parameter is controlled on the basis of the situation information and the dangerous situation. The present technology is not limited thereto, and the control parameter may be controlled in accordance with various situations. For example, a case where the nucleus of the lens has been removed to some degree is assumed. In this case, in a situation where a distance between a piece of the nucleus of the lens and the fragmentation unit 92 is equal to or shorter than a certain distance and they are not in contact with each other, the pressure of aspiration or the amount of aspiration may be relatively increased. Moreover, for example, when the fragmentation unit 92 comes into contact with the piece of the nucleus of the lens, control to decrease the pressure of aspiration or the amount of aspiration may be made.

In the above-mentioned embodiments, the situation information and the dangerous situation are recognized in the image recognition. The present technology is not limited thereto, and the situation information and the dangerous situation may be recognized by any method. For example, the pressure of aspiration and the amount of aspiration in aspirating the waste may be measured and a situation relating to the surgery may be recognized or estimated on the basis of a sensing result. For example, in a case where the posterior capsule is aspirated, the amount of aspiration of the waste is reduced, and therefore the recognition unit 82 may recognize the dangerous situation.

In the above-mentioned embodiments, the maximum value of the control parameter to be output is controlled for each phase. The present technology is not limited thereto, and for example, the maximum value may be controlled in accordance with a distance between the fragmentation unit 92 or the vitreous cutter 142 and a site of the eyeball, such as the retina, which should not be damaged.

FIG. 11 is a block diagram showing a hardware configuration example of the control apparatus 80.

The control apparatus 80 includes a CPU 161, a ROM 162, a RAM 163, an input/output interface 165, and a bus 164 that connects them to one another. A display unit 166, an input unit 167, a storage unit 168, a communication unit 169, a drive unit 170, and the like are connected to the input/output interface 165.

The display unit 166 is, for example, a display device using liquid-crystal, EL, or the like. The input unit 167 includes, for example, a keyboard, a pointing device, a touch panel, and other operation devices. In a case where the input unit 167 includes a touch panel, the touch panel can be integral with the display unit 166.

The storage unit 168 is a nonvolatile storage device and includes, for example, an HDD, a flash memory, and other solid-state memories. The drive unit 170 is, for example, a device capable of driving a removable recording medium 171 such as an optical recording medium and a magnetic recording tape.

The communication unit 169 includes a modem, a router, and other communication devices for communicating with other devices, which are connectable to a LAN, a WAN, and the like. The communication unit 169 may perform wired communication or may perform wireless communication. The communication unit 169 is often used separately from the control apparatus 80.

In the present embodiment, the communication unit 169 enables communication to be performed with other apparatuses via a network.

Software stored in the storage unit 168, the ROM 162, or the like cooperates with hardware resources of the control apparatus 80, thereby realizing information processing of the control apparatus 80 having the above-mentioned hardware configuration. Specifically, loading into the RAM 163 programs that configure the software, which are stored in the ROM 162 or the like, and executing the programs realize an information processing method according to the present technology.

The programs are, for example, installed in the control apparatus 80 via the recording medium 171. Alternatively, the programs may be installed in the control apparatus 80 via a global network or the like. Otherwise, an arbitrary computer-readable non-transitory storage medium may be used.

By cooperation of a computer mounted on a communication terminal with another computer capable of communicating therewith via a network or the like, a control method, a program, and an ophthalmic surgical system according to the present technology are performed and the control apparatus 80 according to the present technology may be built.

That is, the control apparatus, the control method, the program, and the ophthalmic surgical system according to the present technology may be performed not only in a computer system configured by a single computer but also in a computer system in which a plurality of computers cooperatively operate. It should be noted that in the present disclosure, the system means a set of a plurality of components (apparatus, module (parts), and the like) and it does not matter whether or not all the components are housed in the same casing. Therefore, both of a plurality of apparatuses housed in separate casings and connected to one another via a network and a single apparatus having a plurality of modules housed in a single casing are the system.

Performing the control apparatus, the control method, the program, and the ophthalmic surgical system according to the present technology by the computer system includes, for example, both of a case where a single computer performs recognition of the situation information, control of the control parameter, and the like and a case where different computers perform the respective processes. Moreover, performing the respective processes by a predetermined computer includes causing another computer to perform some or all of those processes and acquiring the results.

That is, the control apparatus, the control method, the program, and the ophthalmic surgical system according to the present technology can also be applied to a cloud computing configuration in which a plurality of apparatuses shares and cooperatively processes a single function via a network.

The respective configurations such as the recognition unit and the control unit, the control flow of the communication system, and the like, which have been described with reference to the respective drawings, are merely embodiments, and can be arbitrarily modified without departing from the gist of the present technology. That is, any other configurations, algorithms, and the like for carrying out the present technology may be employed.

It should be noted that the effects described in the present disclosure are merely exemplary and not limitative, and further other effects may be provided. The description of the plurality of effects above does not necessarily mean that those effects are provided at the same time. It means that at least any one of the above-mentioned effects is obtained depending on a condition and the like, and effects not described in the present disclosure can be provided as a matter of course.

At least two features of the features of the above-mentioned embodiments may be combined. That is, the various features described in the respective embodiments may be arbitrarily combined across the respective embodiments.

It should be noted that the present technology can also take the following configurations.

(1) A control apparatus, including:
an acquisition unit that acquires situation information relating to surgery, the situation information being based on a captured image relating to a patient eyeball, the captured image being captured by a surgical microscope; and a control unit that controls a control parameter relating to a treatment apparatus on the basis of the situation information, the treatment apparatus being used for the surgery.

(2) The control apparatus according to (1), in which
the surgery includes at least one of cataract surgery or vitrectomy surgery.

(3) The control apparatus according to (1), in which
the treatment apparatus is a treatment apparatus used for cataract surgery, and
the control parameter includes at least one of a parameter relating to an ultrasonic output, a parameter relating to aspiration through a surgical instrument distal end, and a parameter relating to an inflow of perfusion solution.

(4) The control apparatus according to (1), in which
the treatment apparatus is a treatment apparatus used for vitrectomy surgery, and
the control parameter includes at least one of a parameter relating to a speed of vitreous removal, a parameter relating to aspiration through a surgical instrument distal end, a parameter relating to an inflow of perfusion solution, and a parameter relating to a laser output.

(5) The control apparatus according to any one of (1) to (4), in which
the situation information includes a phase of the surgery, and
the phase includes at least one of cornea portion incision, anterior capsule incision, fragmentation of a lens nucleus, aspiration through the surgical instrument distal end, vitreous removal, and insertion of an intraocular lens.

(6) The control apparatus according to (5), in which
the phase of the fragmentation of the lens nucleus includes a first phase where a predetermined amount or more of the lens nucleus remains and a second phase where a predetermined amount or less of the lens nucleus remains, and
the control unit controls, in the first phase, the parameter relating to the ultrasonic output to be capable of being set to be a predetermined value or less and controls, in the second phase, the parameter relating to the ultrasonic output to be capable of being set to be a limited value less than the predetermined value.

(7) The control apparatus according to any one of (1) to (6), further including
a recognition unit that recognizes the situation information on the basis of the captured image.

(8) The control apparatus according to (7), in which
the recognition unit recognizes a site of the patient eyeball and the treatment apparatus on the basis of the captured image, the site including a lens nucleus, a posterior capsule, a retina, a macula, an optic disc, a cortex, and an affected part, and
the control unit controls the control parameter on the basis of a position of the site and a position of the treatment apparatus that are recognized by the recognition unit.

(9) The control apparatus according to (7) or (8), in which
the control unit controls the parameter relating to the aspiration on the basis of the site and the treatment apparatus that are recognized by the recognition unit.

(10) The control apparatus according to any one of (7) to (9), in which the control unit increases the parameter relating to the aspiration in a case where the recognition unit recognizes that a lens nucleus of the patient eyeball is not in contact with the treatment apparatus.

(11) The control apparatus according to any one of (7) to (10), in which the control unit decreases the parameter relating to the aspiration in a case where the recognition unit does not recognize the cortex in a phase of aspiration through the surgical instrument distal end.

(12) The control apparatus according to any one of (7) to (11), in which the control unit increases a maximum value of the parameter relating to the speed of the vitreous removal in a case where a distance between a position of the posterior capsule or the retina and a position of the treatment apparatus is equal to or longer than a predetermined distance and decreases a maximum value of the parameter relating to the speed of the vitreous removal in a case where the distance between the position of the posterior capsule or the retina and the position of the treatment apparatus is equal to or shorter than the predetermined distance.

(13) The control apparatus according to any one of (7) to (12), in which the control unit controls the laser output on the basis of a position of the macula or a position of the optic disc that are recognized by the recognition unit and a position of an aiming beam emitted from a treatment apparatus used for the vitrectomy surgery.

(14) The control apparatus according to any one of (1) to (13), in which the treatment apparatus includes a sensor unit that acquires sensor information relating to the surgery, and the control unit controls the control parameter on the basis of the sensor information.

(15) The control apparatus according to any one of (7) to (14), further including a presentation unit that presents at least one of the situation information or the control parameter to a user who performs the surgery.

(16) The control apparatus according to (15), in which the recognition unit recognizes a dangerous situation relating to the surgery on the basis of the captured image, and the presentation unit presents the dangerous situation to the user.

(17) A control method, including:

by a computer system acquiring situation information relating to surgery on the basis of a captured image relating to a patient eyeball captured by a surgical microscope; and controls a control parameter relating to a treatment apparatus used for the surgery on the basis of the situation information.

(18) A program that causes a computer system to execute:

a step of acquiring situation information relating to surgery, the situation information being based on a captured image relating to a patient eyeball captured by a surgical microscope; and a step of controlling a control parameter relating to a treatment apparatus used for the surgery on the basis of the situation information.

(19) An ophthalmic surgical system, including:

a surgical microscope capable of capturing an image of a patient eyeball;

a treatment apparatus used for surgery of the patient eyeball; and a control apparatus including an acquisition unit that acquires situation information relating to the surgery, the situation information being based on a captured image relating to the patient eyeball captured by a surgical microscope, and a control unit that controls a control parameter relating to the treatment apparatus on the basis of the situation information.

REFERENCE SIGNS LIST

11 surgical system
21 surgical microscope
80 control apparatus
82 recognition unit
83 control unit
84 GUI presentation unit
90 phacoemulsification machine
96 sensor unit
140 vitrectomy apparatus

The invention claimed is:

1. A control apparatus, comprising:

an acquisition unit configured to acquire a captured image related to a patient eyeball, wherein the captured image is captured by a surgical microscope, and the captured image includes a front image of the patient eyeball and a tomographic image of the patient eyeball;

a recognition unit configured to:

recognize different phases of a surgery of the patient eyeball, based on a type of a surgical instrument, wherein the surgical instrument is associated with the front image of the patient eyeball; and recognize a dangerous situation related to the patient eyeball based on the tomographic image; and a control unit configured to control a control parameter related to a treatment apparatus based on the recognized different phases of the surgery of the patient eyeball and the recognized dangerous situation related to the patient eyeball, wherein the treatment apparatus executes the surgery of the patient eyeball.

2. The control apparatus according to claim 1, wherein the surgery includes at least one of a cataract surgery or a vitrectomy surgery.

3. The control apparatus according to claim 1, wherein the treatment apparatus is for execution of a cataract surgery, and the control parameter includes at least one of a parameter relating to an ultrasonic output, a parameter relating to aspiration through a surgical instrument distal end, or a parameter relating to an inflow of perfusion solution.

4. The control apparatus according to claim 1, wherein the treatment apparatus is for execution of a vitrectomy surgery, and the control parameter includes at least one of a parameter relating to a speed of vitreous removal, a parameter relating to aspiration through a surgical instrument distal end, a parameter relating to an inflow of perfusion solution, or a parameter relating to a laser output.

5. The control apparatus according to claim 1, wherein the different phases of the surgery includes at least one of a phase of a cornea portion incision, a phase of an anterior capsule incision, a phase of a fragmentation of a lens nucleus, a phase of aspiration through a surgical instrument distal end, a phase of a vitreous removal, or a phase of an insertion of an intraocular lens.

6. The control apparatus according to claim 5, wherein the phase of the fragmentation of the lens nucleus includes a first phase and a second phase, in the first phase:

at least a first specific amount of the lens nucleus remains is recognizable, and the control unit is further configured to set a parameter relating to an ultrasonic output to be one of equal to a specific value or less than the specific value, in the second phase:

one of a second specific amount of the lens nucleus remains is recognizable or a third specific amount of the lens nucleus remains is recognizable, wherein the third specific amount of the lens nucleus remains is less than the second specific amount of the lens nucleus remains, the control unit is further configured to set the parameter relating to the ultrasonic output to a limited value, and the limited value is less than the specific value.

7. The control apparatus according to claim 1, wherein the recognition unit is further configured to recognize a site of the patient eyeball and the treatment apparatus based on the captured image, wherein the site of the patient eyeball includes a lens nucleus, a posterior capsule, a retina, a macula, an optic disc, a cortex, and an affected part, and the control unit is further configured to control a position of the recognized site of the patient eyeball and a position of the recognized treatment apparatus.

8. The control apparatus according to claim 7, wherein the control unit is further configured to control a parameter relating to an aspiration through a surgical instrument distal end based on the recognized site and the recognized treatment apparatus.

9. The control apparatus according to claim 1, wherein the recognition unit is further configured to recognize that a lens nucleus of the patient eyeball is contactless with the treatment apparatus, and the control unit is further configured to increase a parameter relating to an aspiration through a surgical instrument distal end based on the recognition that the lens nucleus of the patient eyeball is contactless with the treatment apparatus.

10. The control apparatus according to claim 1, wherein the recognition unit is configured to exclude recognition of a cortex in a phase of an aspiration through a surgical instrument distal end, and the control unit is further configured to decrease a parameter relating to the aspiration based on the exclusion of the recognition of the cortex in the phase of the aspiration through the surgical instrument distal end.

11. The control apparatus according to claim 1, wherein the control unit is further configured to:

increase a maximum value of a parameter relating to a speed of a vitreous removal, in a case where a distance between one of a position of a posterior capsule or a position of a retina and a position of the treatment apparatus is one of equal to a specific distance or longer than the specific distance; and decrease the maximum value of the parameter relating to the speed of the vitreous removal, in a case where the distance between one of the position of the posterior capsule or the position of retina and the position of the treatment apparatus is one of equal to the specific distance or shorter than the specific distance.

12. The control apparatus according to claim 1, wherein the recognition unit is further configured to recognize one of a position of a macula or a position of an optic disc, the control unit is further configured to control a laser output based on one of the position of the macula or the position of the optic disc and a position of an aiming beam, the aiming beam is emitted from the treatment apparatus, and the treatment apparatus is for a vitrectomy surgery.

13. The control apparatus according to claim 1, wherein the treatment apparatus includes a sensor unit configured to acquire sensor information relating to the surgery, and the control unit is further configured to control the control parameter based on the sensor information.

14. The control apparatus according to claim 1, further comprising a presentation unit configured to present at least one of the different phases or the control parameter.

15. The control apparatus according to claim 14, wherein the presentation unit is further configured to present the dangerous situation.

* * * * *